US00PP17204P3

(12) United States Plant Patent
Abrams

(10) Patent No.: US PP17,204 P3
(45) Date of Patent: Nov. 14, 2006

(54) *GERANIUM* PLANT NAMED FAITH

(50) Latin Name: *Pelargonium×hortorum*
Varietal Denomination: Faith

(75) Inventor: Laura B Abrams, Sudbury, MA (US)

(73) Assignee: J P Bartlett Co Inc, Sudbury, MA (US)

( * ) Notice: Subject to any disclaimer, the term of this patent is extended or adjusted under 35 U.S.C. 154(b) by 108 days.

(21) Appl. No.: 10/950,313

(22) Filed: Sep. 27, 2004

(65) Prior Publication Data

US 2006/0070157 P1 Mar. 30, 2006

(51) Int. Cl.
*A01H 5/00* (2006.01)

(52) U.S. Cl. ..... Plt./329

(58) Field of Classification Search ..... Plt./329, Plt./330

See application file for complete search history.

*Primary Examiner*—Wendy Haas

(57) ABSTRACT

This invention is a new and distinct cultivar of a zonal *geranium Pelargonium×hortorum*) named 'Faith' the cultivar has a white centered light lavender pink blossom and medium green foliage on a stable, full, well branched plant.

1 Drawing Sheet

DESCRIPTION

Botanical designation: *Pelargonium×hortorum.*

Variety denomination: 'Faith'.

BACKGROUND OF THE INVENTION

The cultivar was developed from a controlled breeding program conducted at the J. P. Bartlett Company. The company used a non-patented cultivar designated 'Pastel Dot' (#94018) as the male parent and a non-patented cultivar designated 'Pastel Dot' (#94018) as the female parent in a cultivated area to create a single plant 'Faith'. 'Faith's' plant habit is symmetrical with excellent basal branching. The new cultivar 'Faith' differs from its male and female parents (both Pastel Dot) in color shade being darker and with no spots on each petal. Asexual propagation of the new cultivar by cuttings at the location previously stated has shown that the unique features of this new *geranium* are stable and that the plant reproduces true to type in successive generations of asexual propagation.

SUMMARY OF THE INVENTION

The plant's growth habit is compact to medium in vigor. It is a full plant that performs well in both a greenhouse and in a natural environment such as a garden. It will grow more compact under drier conditions but has the ability to be a larger and more vigorous plant with sufficient water and partial shade. The blossoms are tolerant to rain, not turning brown and rotting after a day or so of straight rain. Faith buds early and is consistent with a large and long lasting blossom.

On average, the plant itself can get over 210 millimeters tall, not including the stem or flower. The free branching nature of Faith allows the plants girth to grow and flourish. The width of a single plant is measured to be 347 millimeters and growing. The intensity of the blossom color and strong green leaf color separates itself from any other known to inventor. The semi-double blossom is a lt lavender pink with a darker edge to each petal. 'Faith's' stem is a distinguished lighter green, while the leaf produces a medium darker zone.

'Faith's' standout performance is regarded highly due to it's excellent growth habit, size, blossom and leaf.

The new cultivar of the present invention is being marketed under the BARTLETT'S trademark.

BRIEF DESCRIPTION OF THE PHOTOGRAPH

Accompanying this application is a photographed picture of the plant and its' aspects.

Figure 1:
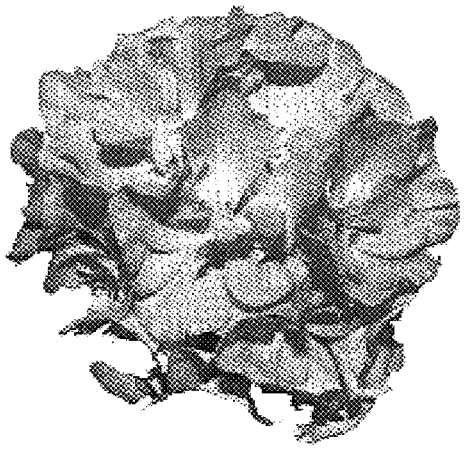

1. FIG. 1 shows the large, semi-double blossom and the light lavender pink color described in the summary.

Figure 2:
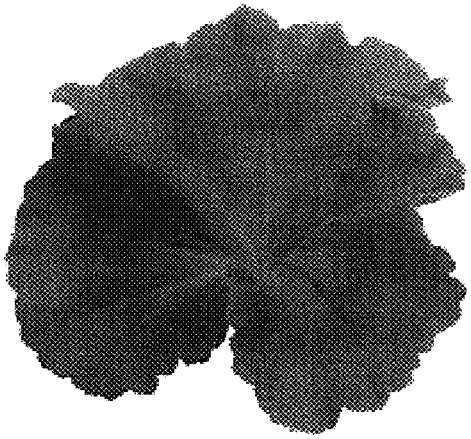

2. FIG. 2 enables us to see the medium green leaf with the medium darker green zone.

Figure 3:
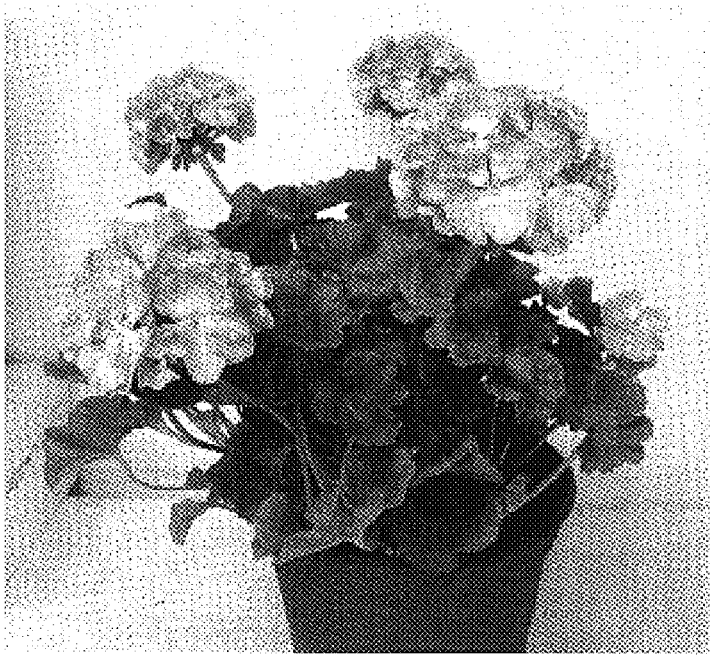

3. FIG. 3 shows the overall plant. This is a single plant from a cutting in a 7.5 inch pot. The height, width, and growth habit are clearly seen here.

DETAILED BOTANICAL DESCRIPTION

The following observations and measurements describe asexual reproductions of 'Faith' grown in greenhouses located in Sudbury, Mass., USA. The plant history was taken on 3 month old plants grown in 7.5" pots, blossomed under natural light in a greenhouse and color readings were taken in the greenhouse in Sudbury, Mass. under ambient light. Color references are primarily to the Pantone Color Selector Chart 1000/coated 1995. The color values were determined on Oct. 22, 2003 under natural light conditions of 200 foot-candles.

Classification:

*Botanical.*—*Pelargonium×hortorum,* cv. 'Faith'.

Inflorescence:

A. Umbel:

*Flowering duration.*—The flowers last approximately 13 to 18 days under standard greenhouse conditions and then dehisce.

*Average diameter.*—Approximately 7.0 to 8.5 cm.

*Average depth.*—Approximately 5.0 to 7.0 cm.

*Peduncle length.*—Approximately 12.0–15.0 cm.

*Peduncle diameter.*—Approximately 0.15 to 0.25 cm.

*Pedicel length.*—Approximately 2.5 to 3 cm.

*Number of umbels per plant.*—When grown in a 7.5" pot at 8 weeks after the sticking of a rooted cutting, there commonly are approximately 7–9 umbels per plant. The umbels form approximately 13 to 16 cm above the foliage.

*Number of florets/umbel.*—When grown in a 7.5" pot at 8 weeks, approximately 27 to 30 florets per umbel commonly are formed.

*Flower depth.*—Approximately 5.15 to 7.4 cm.

B. Corolla: Overall appearance of color, Pantone 236C.

*Buds.*—Elliptical to round in configuration, initially light green and changing to lt. Lavender/pink at the time of opening, and approximately 13 to 16 mm. in length and approximately 6 to 8 mm. in width.

*Peduncle diameter.*—Approximately 0.15 to 0.25 cm.

*Pedicels.*—Commonly approximately 2.5 to 3 cm in length and straight which commonly causes the buds to point substantially upward.

*Average diameter.*—Approximately 4 to 6 cm.

*Form.*—Commonly semi-double with at least two petaloids.

*Petals.*—Spatulate shaped, satiny and smooth. Commonly approximately 7 to 9 petals are present per floret. Petal base is V-shaped with a semi-circular margin. Petal length is approximately 0.83 cm and diameter is approximately 0.34 cm. Upper petal surface is smooth.

*Number of petaloids.*—Commonly forms approximately 2 to 5 petaloids per floret.

*Color.*—General tonality from a distance of three meters: Lt. Lav/Pink.

*Color of upper petals.*—Pantone 236C.

*Markings of upper petals.*—White spot at base of petal.

*Sepals.*—5–7 sepals per floret with a length of approximately 0.3 to 0.7 cm and a width of 0.04 to 0.7 cm. The overall shape is elliptical with V-shaped vase and margin and semi-circular apex. Upper and lower surface are the same texture and color.

C. Reproductive organs:

*Androecium.*—5 fertile anthers, with whitish filaments, orange pollen is located on the lower side of the mature (open) anther. The surface of the anther under the pollen is white.

*Gynoecium.*—5 lobed stigma, Pantone 236C, greenish style, Pantone 368C with one pistil, Pantone 396C per flower.

*Fertility/seed set.*—Commonly does not produce fruits in the absence of mechanical fertilization.

*Spring flowering response period.*—Approximately 5 to 8 weeks from rooted cuttings under standard greenhouse conditions.

*Outdoor flower production.*—Freely flowering under outdoor growing conditions with substantially continuous blooming.

*Durability.*—Ships well.

*Pest/disease resistance/susceptibility.*—No susceptibility to pests or diseases noted to date. Disease resistance has not been tested to date.

Plant:

A. Foliage: Medium green with slight zonation. Zoning color is Pantone 350C. The leaves are pubescent on the upper surface, and smooth on the lower surface.

*Length.*—3.75 to 4.5 cm.

*Width.*—6.5 to 7 cm.

*Form.*—Reniform, with a cordate base.

*Margin.*—Irregularly crenate.

*Ribs and veins.*—Palmate 6.5 to 7 cm. long.

*Leaf color.*—Upper side is Pantone 364C. Under side is Pantone 363C. Leaf upper surface covered predominately with trichomes Pantone 3425C and leaf flower surface is predominately smooth.

*Petioles.*—Commonly approximately 7 to 9 cm long with a diameter of 0.03 to 0.06 cm. Petiole color is Pantone 377C.

A. General appearance and form:

*Internode length.*—Commonly varies from approximately 0.6 to 0.9 cm.

*Branching pattern.*—Freely basal branching as well as lateral branching. No pinching is required to obtain self-branching. A self-branching growth habit is observed in the absence of a growth regulator.

*Height.*—Approximately 27 to 32 cm. above a 7.5" pot at 8 weeks under standard greenhouse conditions.

It is claimed:

1. A new and distinct variety of *geranium* plant as herein illustrated and described.

* * * * *